US010252407B2

(12) United States Patent
Kumar et al.

(10) Patent No.: US 10,252,407 B2
(45) Date of Patent: Apr. 9, 2019

(54) SMART STAPLING DEVICE

(71) Applicant: Wipro Limited, Bangalore (IN)

(72) Inventors: Vijay Kumar, Bangalore (IN); Thomas Chittakattu Ninan, Kannur District (IN); Shagun Rai, Allahabad (IN)

(73) Assignee: Wipro Limited, Bangalore (IN)

( * ) Notice: Subject to any disclaimer, the term of this patent is extended or adjusted under 35 U.S.C. 154(b) by 72 days.

(21) Appl. No.: 15/281,989

(22) Filed: Sep. 30, 2016

(65) Prior Publication Data

US 2018/0050446 A1 Feb. 22, 2018

(30) Foreign Application Priority Data

Aug. 18, 2016 (IN) .............................. 201641028174

(51) Int. Cl.
*B25C 5/16* (2006.01)
*B25C 5/02* (2006.01)
(Continued)

(52) U.S. Cl.
CPC ........ B25C 5/1689 (2013.01); A61B 17/0686 (2013.01); B25C 5/025 (2013.01);
(Continued)

(58) Field of Classification Search
CPC .............................. B25C 5/1689; B25C 5/025
(Continued)

(56) References Cited

U.S. PATENT DOCUMENTS 5,320,335 A * 6/1994 Iwata ........................ B42B 4/00
270/52.02
5,992,724 A * 11/1999 Snyder .................. B25C 5/1689
227/120

(Continued)

FOREIGN PATENT DOCUMENTS

| DE | 10 2006 046 842 | 4/2008 |
| WO | WO 2009/078808 | 6/2009 |
| WO | WO 2011/129736 | 10/2011 |

OTHER PUBLICATIONS http://nif.org.in/innovation/stapler-that-indicates-pin-are-finishing/545, "Stapler that indicates pin are finishing", 2 pages.
(Continued)

*Primary Examiner* — Ricky Ngon
(74) *Attorney, Agent, or Firm* — Finnegan, Henderson, Farabow, Garrett & Dunner LLP

(57) ABSTRACT

The present disclosure discloses a stapling device, comprising an activation unit configured to sense at least one of a movement of the stapling device, a position of a switch or a signal from a timer. There is a detection unit that is activated based on a signal from the activation unit to generate an input data. The stapling device further comprises a processing unit to determine number of pins in the stapling device, by comparing the input data with a pre-configured data and a display unit interfaced with the processing unit, to indicate status of the pins in the stapling device, wherein the status is based on the determined number of pins in the stapling device. Thus the stapling device of the present
(Continued)

disclosure identifies the exhaustion of pins and accordingly enables timely replenishment of the stapling device with pins.

16 Claims, 4 Drawing Sheets

(51) Int. Cl.
*A61B 17/068* (2006.01)
*A61B 90/00* (2016.01)

(52) U.S. Cl.
CPC .............. *A61B 2090/0803* (2016.02); *A61B 2090/0807* (2016.02)

(58) Field of Classification Search
USPC ........................................................ 702/189
See application file for complete search history.

(56) References Cited

U.S. PATENT DOCUMENTS

| | | | | |
|---|---|---|---|---|
| 6,062,454 A * | 5/2000 | Morishige | ............ | B25C 5/1689 227/1 |
| 6,955,281 B1 * | 10/2005 | Wei | ...................... | B25C 5/1689 227/120 |
| 8,701,956 B2 * | 4/2014 | Takemura | ............... | B25B 21/00 227/131 |
| 9,757,128 B2 * | 9/2017 | Baber | .............. | A61B 17/07207 |
| 2003/0029875 A1 * | 2/2003 | Sesek | ........................ | B27F 7/17 220/589 |
| 2003/0102618 A1 * | 6/2003 | Sesek | ........................ | B27F 7/17 270/58.08 |
| 2004/0212135 A1 * | 10/2004 | Obregon | ............... | B25C 5/1689 270/58.08 |
| 2005/0242149 A1 * | 11/2005 | Higuchi | ................ | B25C 5/1689 227/2 |
| 2008/0110652 A1 | 5/2008 | Wen | | |
| 2008/0179371 A1 * | 7/2008 | Gardner | .................... | B25C 5/15 227/1 |
| 2009/0077278 A1 * | 3/2009 | Kuroda | ............. | H04N 1/00323 710/58 |
| 2009/0194574 A1 * | 8/2009 | Shima | ....................... | B25C 1/06 227/136 |
| 2011/0093110 A1 | 4/2011 | Stencel et al. | | |
| 2012/0223121 A1 * | 9/2012 | Viola | ................... | A61B 17/072 227/175.1 |
| 2016/0096700 A1 * | 4/2016 | Suzuki | ................... | B65H 37/04 412/1 |

OTHER PUBLICATIONS

Extended European Search Report from the European Patent Office in counterpart European Application 16196191.7 dated Jun. 19, 2017, 9 pages.

\* cited by examiner

SMART STAPLING DEVICE

TECHNICAL FIELD

The present disclosure generally relates to field of mechanical joining devices. Particularly, but not exclusively the present disclosure relates to a stapling device. Further embodiments of the present disclosure disclose a smart stapling device and a method for determining stock of pins in the stapling device.

BACKGROUND

Stapling device as known in the art is a mechanical device used to bind together two or more objects such as plurality of leaf of papers, by employing metal staples or pins. The metal staples or pins will be stored in the stapling device and a force will be applied to penetrate staples or pins into the objects from one side. The staples or pins after passing through the stack of objects will be bent as a result of being stopped by the staple base on the other side. The stapling device may also be used in medical applications, for example in surgical procedures to close skin wounds, connect or remove parts etc. The stapling device is thus an important part of office appliances, schools, and hospital appliances for fastening papers or documents and for surgical procedures respectively. It happens many a times that user would not know the stock of staples or pins in the stapler, and when the user wants to use the stapling device, the user would find that the stapling device is empty. This is an uncomfortable experience and also leads to wastage of time to look for the pins. In work places and offices, generally stationaries are maintained by a particular team and information about the pin outage in the stapling device might not reach the concerned team in time. Hence, this causes inconvenience and is also uneconomical particularly for an organization that has a large number of personnel.

In an attempt to remedy this problem, conventionally several ways have been proposed. One such solution is coloring, last few pins in the stack of pins are made of a different color. With this solution, the user may identify that the pins are getting over in the stapler device, when the pins of different color appear while stapling. Accordingly, the user may replenish the stapler with new set of pins.

In another conventional approach, body of the stapling device maybe made of a transparent material such as glass, so that the user would notice the exhaustion of pins and replace it with new set of pins for further usage.

However, these conventional approaches require manual intervention from the user and depend on attention of the user which varies from user to user. For instance, if the user fails to notice exhaustion of pins, solution to the problem would not be arrived at. Also, the conventional approaches fail to address situations such as office premises where stationaries are maintained by particular team. Thus the conventional or existing approach cannot be seen as a fool-proof solution to the problem.

Therefore, there exists a need for the stapling device which addresses one or more limitations stated in the foregoing paragraphs.

SUMMARY

One or more shortcomings of the prior art are overcome and additional advantages are provided through the present disclosure. Additional features and advantages are realized through the techniques of the present disclosure. Other embodiments and aspects of the disclosure are described in detail herein and are considered a part of the claimed disclosure.

In one non limiting embodiment of the disclosure, a stapling device has been disclosed. The stapling device comprises an activation unit configured to sense at least one of a movement of the stapling device, a position of a switch or a signal from a timer. In the stapling device, there is a detection unit communicatively coupled to the activation unit, the detection unit is activated based on a signal from the activation unit to generate an input data. The stapling device further comprises a processing unit to determine number of pins in the stapling device. The processing unit compares the input data with a pre-configured data to determine the number of pins. Further, a display unit is provided in the stapling device, and is interfaced with the processing unit, to indicate status of the pins in the stapling device, wherein the status is based on the determined number of pins in the stapling device.

In another non limiting embodiment of the disclosure, there is provided a method for monitoring status of pins in a stapling device. The method comprises activating, by a processing unit of the stapling device, a detection unit upon receiving a signal from an activation unit to generate an input data. The signal is generated when the activation unit senses at least one of a movement of the stapling device, a position of a switch or a signal from a timer. The method further comprises determining, by the processing unit, number of pins in the stapling device by comparing the input data with a pre-configured data. Furthermore, the method comprises indicating, on a display unit of the stapling device, interfaced with the processing unit, status of pins in the stapling device. The status is based on the determined number of pins in the stapling device.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE ACCOMPANYING FIGURES

The accompanying drawings, which are incorporated in and constitute a part of this disclosure, illustrate exemplary embodiments and, together with the description, serve to explain the disclosed principles. In the figures, the left-most digit(s) of a reference number identifies the figure in which the reference number first appears. The same numbers are used throughout the figures to reference like features and components. Some embodiments of system and/or methods in accordance with embodiments of the present subject matter are now described, by way of example only, and with reference to the accompanying figures, in which:

Figure 1A:
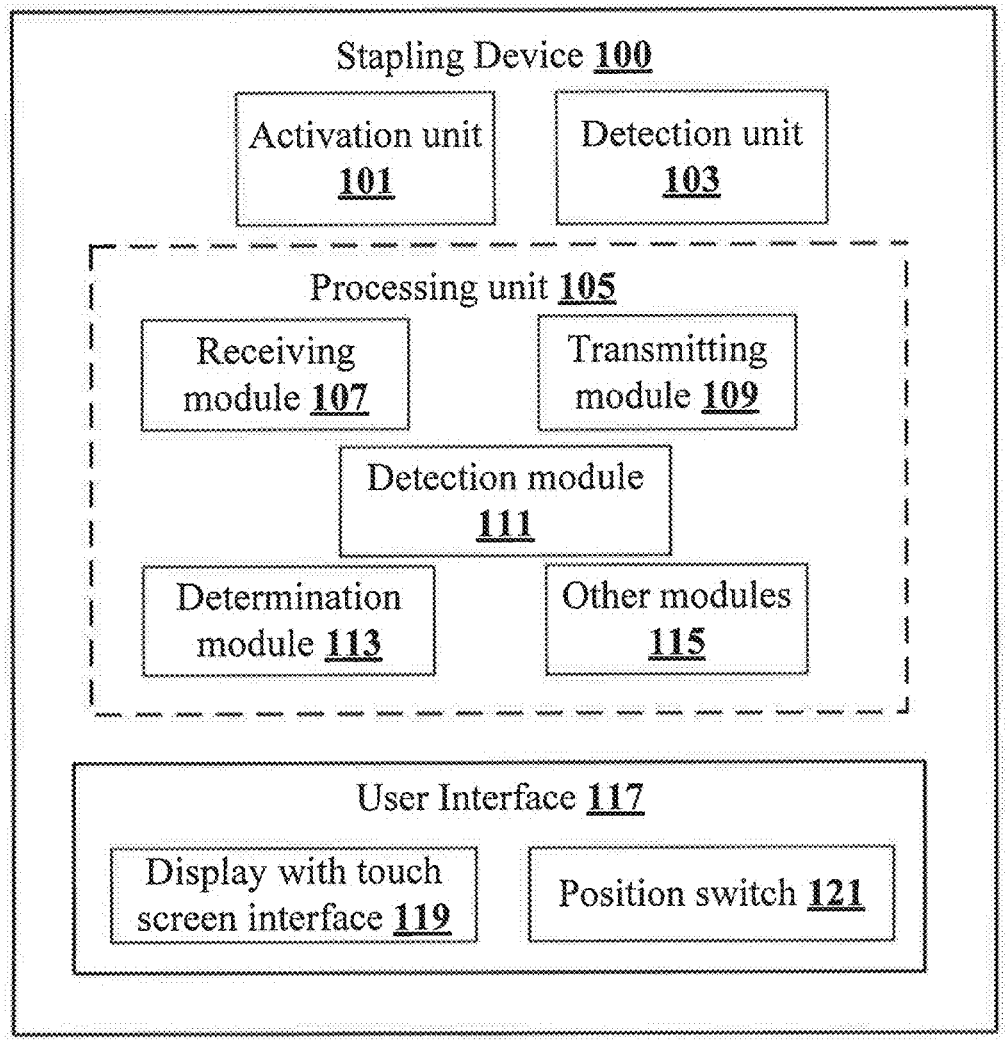
FIGS. 1A and 1B show a detailed block diagram illustrating a stapling device for monitoring status of pins in the stapling device in accordance with some embodiments of the present disclosure.

It should be appreciated by those skilled in the art that any block diagrams herein represent conceptual views of illustrative device embodying the principles of the present subject matter. Similarly, it will be appreciated that any flow charts, flow diagrams, state transition diagrams, and the like represent various processes which may be substantially represented in computer readable medium and executed by a computer or processor, whether or not such computer or processor is explicitly shown.

DETAILED DESCRIPTION

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiment thereof has been shown by way of example in the drawings and will be described in detail below. It should be understood, however that it is not intended to limit the disclosure to the particular forms disclosed, but on the contrary, the disclosure is to cover all modifications, equivalents, and alternative falling within the spirit and the scope of the disclosure.

The terms "comprises", "comprising", or any other variations thereof, are intended to cover a non-exclusive inclusion, such that a setup, device or method that comprises a list of components or steps does not include only those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or method.

The present disclosure discloses a smart stapling device which is configured with a method to monitor status of pins in the stapling device. This enables timely replenishment of the stapling device with pins. Thus, the user would be able to identify status of the stapling device and accordingly decide if replenishment of stapling device is necessary.

The stapling device of the present disclosure comprises a stapling body of known configuration, having an arm, base and a carrier. The carrier of the stapling body is configured to accommodate a stack of pins or staples and when a certain amount of force is applied by the user on the stapling body, the pins bind the objects. Further, the stapling device comprises an activation unit configured to sense at least one of movement of the stapling device, position of a switch provisioned in the stapling device or a signal from the timer. The stapling device further comprises a processing unit which is communicatively coupled to the activation unit. The processing unit is configured to activate detection unit of the stapling device which generates an input data upon receiving a signal from the activation unit. In an embodiment of the disclosure, the detection unit of the stapling device is at least one of image capturing unit or one or more sensors. In an embodiment, the image capturing unit is a camera and one or more sensors include variable resistor sensor and proximity sensor. In an embodiment, the input data from the detection unit includes images of the pins captured by the image capturing unit and signals from the variable resistor sensor and proximity sensor. The processing unit is further configured to determine the status of pins in the stapling device by comparing the input data received from the detection unit with a pre-configured data stored in a memory unit of the stapling device. In an embodiment, status of the pins includes number of pins in the stapling device. The stapling device further comprises a display unit interfaced with the processing unit to indicate the status of the pins in the stapling device.

In an embodiment of the disclosure, the input data generated by the image capturing unit includes images of the stack of pins, and these images are compared with pre-stored images of the stack of pins by the processing unit to determine the status of the pins in the stapling device. Further, the input data generated by variable resistor sensor corresponds to variation in resistance value due to the movement of pin slider in the stapling device. Accordingly, as and when the pins are used, the pin slider of the stapling device moves and the variable resistor sensor configured senses the movement and transmits the signal corresponding to variation of resistance to the processing unit. The processing unit upon receipt of periodical signals from the variable resistor sensor compares the input resistance with the pre-configured resistance values stored in the memory unit. The processing unit then computes the change in resistance because of the movement of the pin slider and accordingly determines the status or number of pins in the stapling device. In an embodiment, the processing unit determines the status of the pins in the stapling device using signals from the proximity sensor. The proximity sensor transmits signal to the processing unit, once the slider moves out of range implying that the number of pins are reducing. The processing unit processes the signal received from the proximity sensor and by comparing it with the pre-configured data, the processing unit determines the status or the number of pins in the stapling device.

In an embodiment of the disclosure, the processing unit is configured to detect the location of the stapling device using an Indoor Positioning System (IPS). The stapling device has a communication interface, which communicates the status of the stapling device and the location of the user to one or more external devices. The external devices may be handled by an administration team or maintenance personnel where there is possession of stocks of pins. The administration team intercepts the message received through external devices and replenishes the stapling device with pins for further usage by the users.

In the following detailed description of the embodiments of the disclosure, reference is made to the accompanying drawings that form a part hereof, and in which are shown by way of illustration specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense.

Figure 1B:
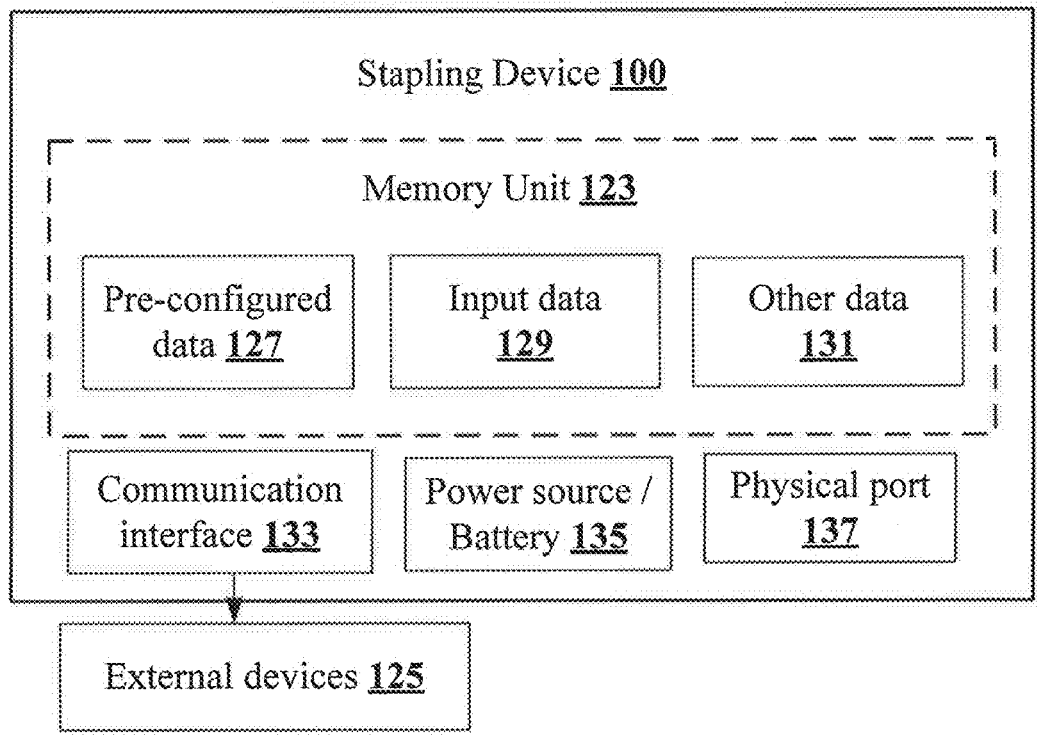

FIGS. 1A and 1B show a detailed block diagram of a stapling device for monitoring the status of staples or pins in the stapling device in accordance with some embodiments of the present disclosure.

In an exemplary implementation, as shown in FIG. 1A, the stapling device 100 comprises an activation unit 101, detection unit 103, processing unit 105 and a user interface 117.

As shown in FIG. 1A, the stapling device 100 is provided with an accelerometer, switch (not shown in the figure) and timer (not shown in the figure). The activation unit 101 provisioned in the stapling device 100 is configured to sense at least one of movement of the stapling device 100 through accelerometer, position of the switch or signal from the timer. Upon sensing at least one of the above by the activation unit 101, a detection unit 103 of the stapling device 100 which is interfaced with the activation unit 101 is activated and the activation of the detection unit 103 is done by the processing unit 105. By selectively activating the detection unit 103, power drawn from power source 135 configured in the stapling device 100 is optimized and a substantial amount of power is conserved. In an embodiment, accelerometer is used to sense movement of the stapling device 100 and the detection unit 103 begins to perform its function when there is a movement of the stapling device 100. In another embodiment, the detection unit 103 may be activated with the help of a switch, wherein, when position of the switch is towards 'on', activation of detection unit 103 is triggered and when 'off', detection unit 103 doesn't perform its function, thus conserving power of the battery 135. Therefore, according to the user requirement and power source 135 power level, the position of the switch can be turned 'on' or 'off'. In yet another embodiment, detection unit 103 of the stapling device 100 is activated by the activation unit 101 based on the signal received from the timer associated with the processing unit 105. With the help of timer, the processing unit 105 may activate the detection unit 103 upon reaching pre-set time limit to perform its function. This ensures periodic monitoring of the status of the pins in the stapling device 100.

In an embodiment, the detection unit 103 is communicatively coupled to the activation unit 101 and the processing unit 105. The detection unit 103 is at least one of an image capturing unit 103a or one or more sensors 103b and 103c. In an embodiment, the one or more sensors includes a variable resistor sensor 103b and a proximity sensor 103c. The detection unit 103 is activated by the processing unit 105 when the activation unit 101 senses at least one of movement of the stapling device 100, position of the switch or signal from the timer. The detection unit 103 is configured to generate input data which is transmitted to the processing unit 105 for further processing.

The image capturing unit 103a will be positioned proximal to stack of pins of the stapling device 100 and is configured to capture images of the pins and is transmitted to a memory unit 123 associated with the processing unit 105. In an embodiment, the image capturing unit 103a is a wide angle camera. The image capturing unit 103a periodically captures the images of the pins of the stapling device 100 and transmits it to the memory unit 123 for further processing by the processing unit 105. Further, the variable resistor sensor 103b comprises a brush (not shown in the figure) which is configured to slide along with the pin slider of the stapling device 100. As the pin slider moves when the pins are used, the brush of the variable resistor sensor 103b senses the change in resistance. The variable resistor sensor 103b is connected to the analog to digital converter ports of the processing unit 105 and periodically sends the signal corresponding to change in resistance due to movement of the pin slider, which is processed by the processing unit 105. Thus the variable resistor sensor 103b helps in identifying the position of the pin slider. In yet another embodiment, the proximity sensor 103c may be used to identify the position of the pin slider [shown in FIG. 2] in the stapling device 100. The proximity sensor 103c sends signals to the processing unit 105 corresponding to proximity of the pin slider from a reference point in stapling device 100 and assist in determining number of pins in the stapling device 100.

The user interface 117 includes a display with touch screen interface 119 and a position switch 121. In an embodiment, the display with touch screen interface 119 may be used to display information related to the stapling device 100. The information includes status of pins in the stapling device 100, which may be in the form of remaining stock or number of pins in the stapling device 100, percentage of battery 135 remaining in the stapling device 100, alert signal to indicate that the pins in the stapling device 100 are getting over, location of the stapling device 100, model information of the stapling device 100 etc. In another embodiment, the display with touch screen interface 119 may be configured to receive one or more inputs from the user of the stapling device 100. As an example, the inputs received from the users may include, but not limited to, the pre-configured data 127 related to the stapling device 100.

The processing unit 105 may include, but not limited to, a receiving module 107, a transmitting module 109, a detection module 111, a determination module 113 and one or more other modules 115. The memory unit 123 may be communicatively coupled to the processing unit 105 stores pre-configured data 127 such as images of the pins in the stapling device 100. In an embodiment, the pre-configured data 127 includes number of pins in the stapling device 100 for a particular change in resistance value or for a particular resistance value. In another embodiment, pre-configured data 127 includes number of pins for a certain range of proximity of the pins from a reference in the stapling device 100. The memory unit 123 is also configured to store the input data 129, it receives from the image capturing unit 103a and the one or more sensors 103b and 103c. In an embodiment, the memory unit 123 stores any other information related to the stapling device 100 in the form of other data 131.

In one embodiment, the data may be stored in the memory unit 123 in the form of various data structures. Additionally, the aforementioned data can be organized using data models, such as relational or hierarchical data models. The other data 131 may store data including temporary data and temporary files, generated by modules for performing the various functions of the stapling device 100.

In an embodiment, the receiving module 107 is configured to receive one or more signals and input data 129 from the one or more modules of the stapling device 100. As an example, the receiving module 107 may receive signals from the position switch 121 for activating the detection unit 103 of the stapling device 100. In an embodiment, the transmitting module 109 may transmit one or more control signals from the processing unit 105 to one of the one or more modules of the stapling device 100. As an example, the transmitting module 109 may transmit one or more images of the pins in the stapling device 100, captured by the image capturing unit 103a, to the determination module 113. In an embodiment, the transmitting module 109 also transmits signals from the variable resistor sensor 103b and signals from proximity sensor 103c to the determination module 113.

In an embodiment, the determination module 113 determines the number of pins in the stapling device 100. The determination module 113 determines the number of pins using the input data 129 received from the image capturing unit 103a and the one or more sensors 103b and 103c. The determination module 113 compares the images captured by the image capturing unit 103a with the pre-configured images of the pins stored in the memory unit 123. With this comparison, the determination module 113 determines the number of pins in the stapling device 100. In another embodiment, the determination module 113 determines the number of pins by identifying the pin slider position. The pin slider position may be determined by variable resistor sensor 103b, wherein, as and when there is a change in the pin slider position, the resistance value input to the processing unit 105 by the variable resistor sensor 103b varies. In an embodiment, the pre-configured data 127 includes data related to number of pins in the stapling device 100 for a corresponding change in resistance value. This way, with the help of variable resistor sensor 103b, remaining stock or number of pins in the stapling device 100 is determined by the determination module 113. In another embodiment, the determination module 113 determines the pin slider position and further number of pins in the stapling device 100 by using proximity sensor 103c. The proximity sensor 103c sends a signal to the processing unit 105, once the pin slider moves in the stapling device 100. A reference point of the pin slider may be pre-configured in the memory unit 123 in the form of pre-configured data 127. In an embodiment, the pre-configured data 127 may include number of pins based on the proximity of the pin slider and when the proximity signal by the proximity sensor 103c, is transmitted to the processing unit 105, the determination module 113 would compare the received signal with the pre-configured data 127 and determine the number of pins in the stapling device 100. In an embodiment, the detection module 111 may be used for detecting location of the stapling device 100. In an embodiment, Indoor Positioning System (IPS) may be used to determine the location of the stapling device 100. The IPS is a system that may locate objects inside a building using radio waves, magnetic fields, or other sensory information.

In an alternative implementation, the stapling device 100, in addition to components disclosed in FIG. 1A, comprises a memory unit 123, a communication interface 133, one or more physical ports 137, a power source 135 and external devices 125 as shown in FIG. 1B. In an embodiment, the communication interface 133 may include, but not limited to, a wireless communication technique such as Bluetooth, Near Field Communication (NFC) and Wi-Fi. The communication interface 133 configured in the stapling device 100 may be used to perform one or more actions including transmission of one or more information, related to the stapling device 100, to the external devices 125 which may be handled by maintenance personnel. The one or more information communicated by the communication interface 133 to the external devices 125 include the number of pins in the stapling device 100, the alert signal to indicate exhaustion of pins in the stapling device 100 and the location of the stapling device 100. In an embodiment, the alert signal is indicated on the display unit 119 when a pre-determined number of pins are used. Thus alert signal is an indication that the stapling device 100 is to be replenished with pins for further usage. In another embodiment, the communication interface 133 may further include one or more localization techniques including Wi-Fi triangulation and Wi-Fi fingerprinting. The localization techniques may be used for detecting location of the stapling device 100.

In an embodiment, the stapling device 100 may comprise a physical port 137 used for configuring the stapling device 100 with one or more pre-configured data 127. As an example, the pre-configured data 127 comprises at least one of the location of the stapling device 100, model information of the stapling device 100, images of the pins in the stapling device 100, number of pins corresponding to the pin slider position or resistance, number of pins corresponding to the proximity of the pins in the stapling device 100. In another embodiment, the physical port 137 may be used for charging the battery 135 of the stapling device 100.

Figure 2:
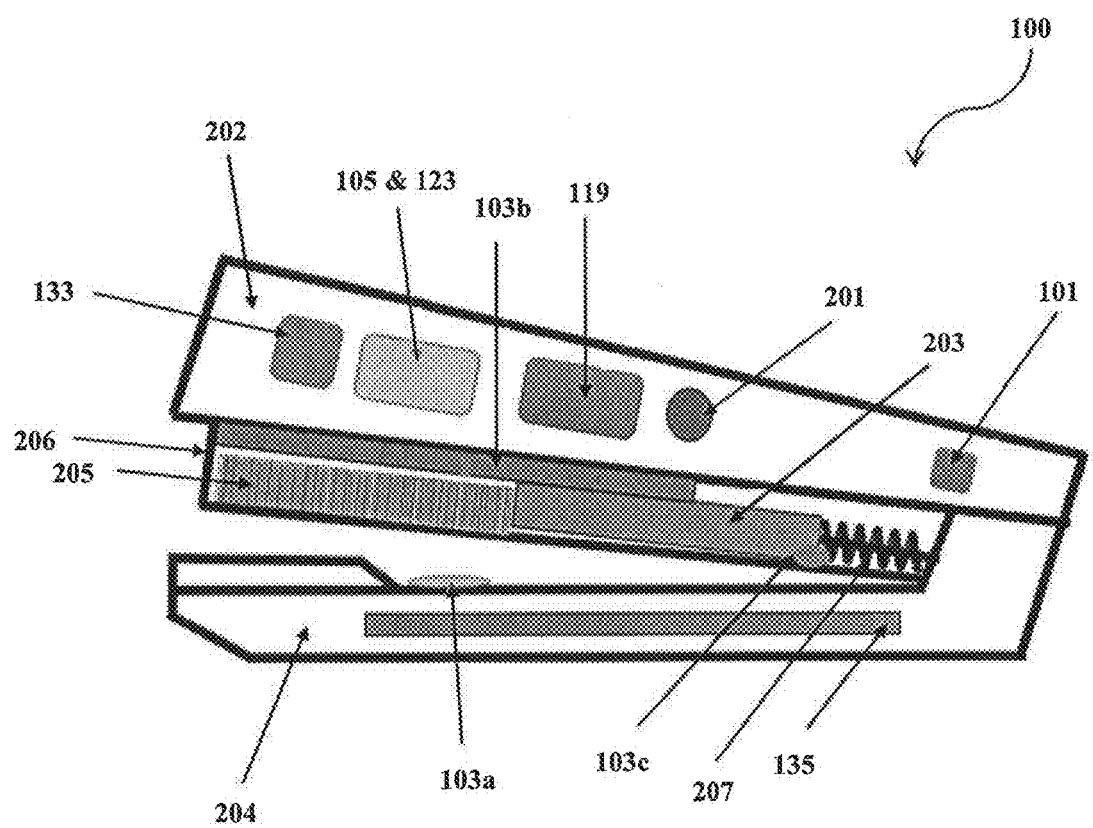
FIG. 2 shows exemplary representation of the stapling device in accordance with some embodiments of the present disclosure.

FIG. 2 shows exemplary representation of the stapling device 100 in accordance with some embodiments of the present disclosure.

As shown in FIG. 2 the stapling device 100 comprises a stapling body of known configuration, having an arm 202, a base 204 and a carrier 206. The carrier 206 of the stapling body is configured to accommodate a stack of pins 205 or staples. In an embodiment, the arm 202 forms the upper portion of the stapling body and base 204 forms a lower portion of the stapling body. In an embodiment of the disclosure, the pin slider 203 is configured with a spring 207 to maintain the tension on a pin slider 203 to move the stack of pins 205 towards the punch during operation. In one embodiment, arm 202 of the stapling device 100 is configured with a plurality of components including, but not limited to activation unit 101, a user input button 201, a display unit 119, a processing unit 105, a memory unit 123 and a communication interface 133. Further, a variable resistor sensor 103b is configured in the stapling device 100 such that the movement of the pin slider 203 will move the brush of the variable resistor sensor. Further, at least one proximity sensor 103c is provisioned at one end of the pin slider 203. In an embodiment, the stapling device 100 comprises an image capturing unit 103a to capture the images of the pins 205. The base 204 of the stapling device 100 comprises a power source 135 such as battery which provides necessary power for functioning of the stapling device 100.

The activation unit 101 of the stapling device 100 is configured to sense the movement of the stapling device 100, position of the switch (not shown in the figure) and signal from a timer (not shown in the figure). Upon sensing any of these, the activation unit 101 sends a signal to the processing unit 105 which activates the detection unit 103. In an embodiment, movement of the stapling device 100 is sensed by an accelerometer. In an embodiment, the detection unit 103 is activated when the position of the switch is towards 'on' and the detection unit 103 may also be activated after completion of a pre-determined time period. Thus by selectively activating the detection unit 103, power of the battery 135 is utilized optimally. The detection unit 103 includes image capturing unit 103a such as camera which captures images of the pins 205 in the stapling device 100 and is transmitted to the memory unit 123. The memory unit 123 would also comprise pre-stored images of the pins 205. The processing unit 105 associated with the memory unit 123 analyzes the captured images of the pins 205 with the pre-stored images of the pins 205 and determines the number of pins 205 remaining in the stapling device 100.

In an embodiment, the position of the pin slider 203 and thus number of pins 205 in the stapling device 100 may also be determined by the one or more sensors, which include variable resistor sensor 103b and proximity sensor 103c. The variable resistor sensor 103b comprises a brush which is configured to slide along the pin slider 203 as the pins are used. The change in resistance occurs when the pin slider 203 moves up when the pins 205 are utilized. The processing unit 105 reads the change in resistance by comparing the signal from the variable resistor sensor 103b with the pre-configured data and determines the number of pins 205 in the stapling device 100. As an example, the pre-configured data may include resistance value of one ohm corresponding to each pin in the stack of pins of the stapling device 100. Now considering the stack of pins of fifty, then the total resistance value would be fifty ohms. When, each pin of the stack of pins are used, a variation in resistance of one ohm will be sensed by the variable resistance sensor, during which the processing unit 105 reads the signal from the variable resistor sensor 103b. Further the processing unit 105 analyzes the signal to compute the resistance change and accordingly determines the number of pins 205 by comparison with the pre-configured data. In another embodiment, the position of the pin slider 203 and thus number of pins 205 may be determined by proximity sensor 103c. The proximity sensor 103c sends signals to the processing unit 105 once the pin slider 203 moves out of range from a reference point in the stapling device 100 as the pins are getting over. The processing unit 105 compares this signal with the pre-configured data related to the proximity of pins 205 from a reference point and determines the number of pins 205 in the stapling device 100. As an example, the pre-configured data may include number of pins 205 based on the distance from the reference point. Considering that, initially when the stack of pins is full, the distance of the reference point from the proximity sensor is 20 millimeters. Accordingly, when the pins are used, there may be a change in the distance (say 0.5 millimeter decrease for each pin usage), during which the processing unit 105 reads the signal from the proximity sensor 103c. Further the processing unit 105 analyzes the signal to compute the change in distance and accordingly determines the number of pins 205 by comparison with the pre-configured data. In an embodiment of the disclosure, the proximity sensor may be at least one of inductive, magnetic, capacitive and photo electric sensor.

In an embodiment, the display unit 119 is configured to indicate the status of the pins in the stapling device 100. In one embodiment the display unit 119 indicates the number of pins 205 remaining in the stapling device 100 as determined by the processing unit 105 or it could be an illuminating device like a LED which may also indicate an alert signal once the pins 205 are less than a preset value. In another embodiment, the stapling device 100 has a communication interface 133 to communicate the status of the pins 205 to one or more external devices. Thus through the external devices, maintenance personnel would be notified about the status of the pins, and accordingly the stapling device 100 may be replenished with pins 205 for further usage.

In an embodiment, the user input button 201 allows the user of the stapling device 100 to notify one or more maintenance personnel about the status of the stapling device 100 through the external devices 125. The maintenance personnel may perform appropriate actions upon receiving the notification from the user. The actions performed by the maintenance personnel may include, but not limited to, replenishing the stapling device 100 with pins 205 and charging the battery 135 of the stapling device 100.

Figure 3:
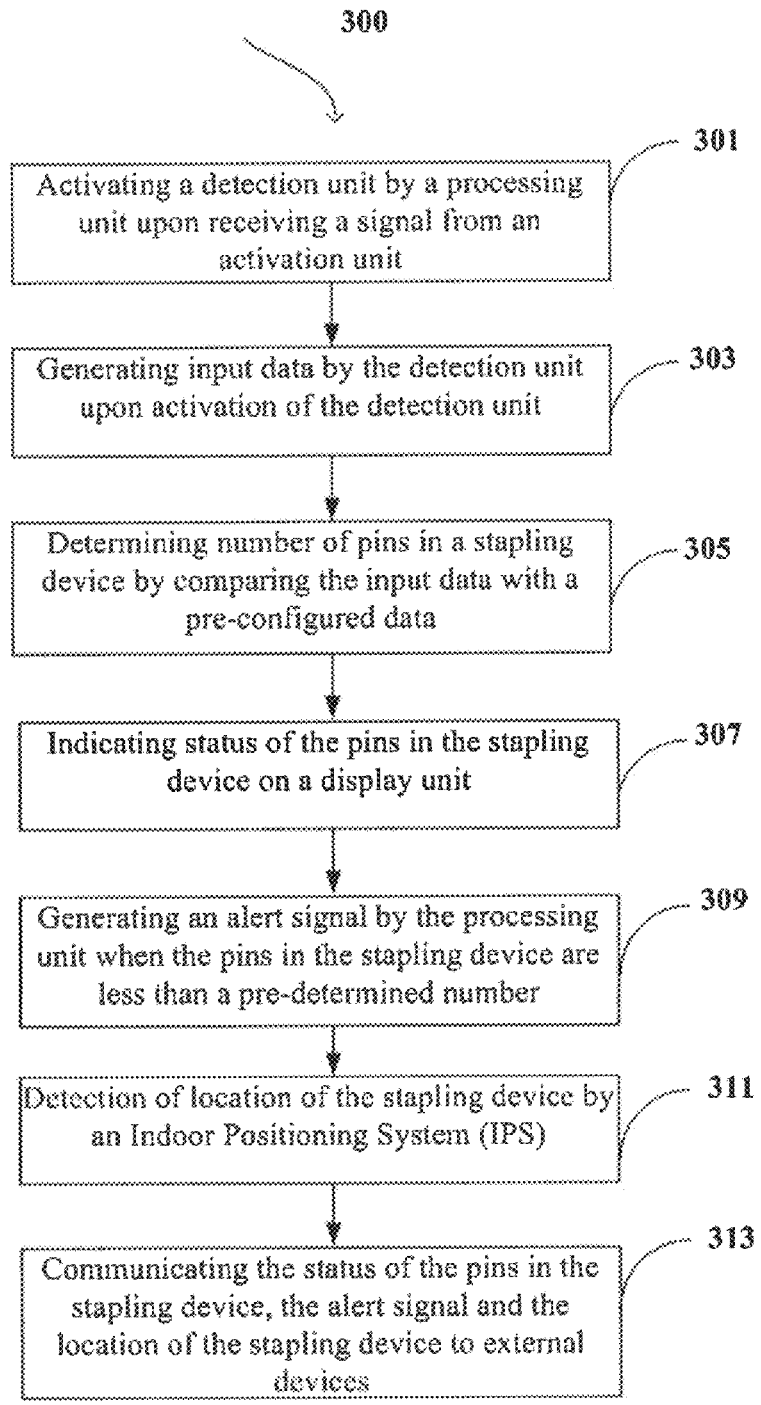
FIG. 3 illustrates a flowchart showing method for monitoring status of pins in the stapling device in accordance with some embodiments of the present disclosure.

FIG. 3 illustrates a flowchart showing method for determining and monitoring status or number of pins in the stapling device 100 in accordance with some embodiments of the present disclosure.

As illustrated in FIG. 3, the method 300 comprises one or more blocks for determining the number of pins in the stapling device 100. The method 300 may be described in the general context of computer executable instructions. Generally, computer executable instructions can include routines, programs, objects, components, data structures, procedures, modules, and functions, which may perform particular functions or implement particular abstract data types.

The order in which the method 300 is described is not intended to be construed as a limitation, and any number of the described method blocks can be combined in any order to implement the method. Additionally, individual blocks may be deleted from the methods without departing from the spirit and scope of the subject matter described herein. Furthermore, the method can be implemented in any suitable hardware, software, firmware, or combination thereof.

At block 301, the detection unit 103 of the stapling device 100 is activated by the processing unit 105 upon receiving a signal from the activation unit 101. In an embodiment, the activation unit 101 sends the signal to the processing unit 105 to activate the detection unit 103 when it senses movement of the stapling device 100 or when the position of the switch is 'on'. In an embodiment, the detection unit 103 is activated by the processing unit 105 after passage of a pre-determined time period, wherein detection unit 103 is activated when the activation unit 101 receives signal from the timer configured in the stapling device 100. In an embodiment, the pre-determined time period maybe input by the user to store it in the memory unit 123 as part of the pre-configured data 127.

At block 303, upon activation of the detection unit 103 by the processing unit 105, the detection unit 103 generates input data 129. In an embodiment, the detection unit 103 includes image capturing unit 103a and one or more sensors 103b and 103c. The one or more sensors includes variable resistor sensor 103b and proximity sensor 103c. Thus the input data 129 generated by the detection unit 103 includes images captured by the image capturing unit 103a, signal corresponding to change in resistance as the pin slider moves up and signal to determine proximity of the pins from a reference in the stapling device 100.

At block 305, the processing unit 105 upon receipt of the input data 129 from the detection unit 103, determines the status of the pins in the stapling device 100, which corresponds to the number of pins in the stapling device 100. The determination of the number of pins in the stapling device 100 is done by comparing the input data 129 with a pre-configured data 127 stored in the memory unit 123. In an embodiment, the processing unit 105 analyses the images of the pins in the stapling device 100 captured by the image capturing unit 103a and compare it with pre-stored images of the pins. This way the number of pins in the stapling device 100 is determined. In another embodiment, the processing unit 105 compares input resistance by the variable resistor sensor 103b with a pre-configured resistance in the pre-configured data 127 and determines the number of pins in the stapling device 100. In yet another embodiment, processing unit 105 compares the input signal by the proximity sensor 103c with the pre-configured data 127 corresponding to proximity of the pins from a reference in the stapling device 100 and determines the number of pins in the stapling device 100.

At block 307, the display unit 119 of the stapling device 100 is configured to display the status of the pins in the stapling device 100, the status may be displayed in the form of number of pins in the stapling device 100.

At block 309, the processing unit 105 may generate an alert signal when the pins in the stapler device 100 are determined to be less than a pre-determined number. The alert signal may be indicated on display unit which acts as an indication to the user that the pins in the stapler device are less and the stapling device is to be replenished with new set of pins for further usage by the user.

At block 311, the processing unit 105 of the stapling device 100 also detects the location of the user. In an embodiment, the location of the stapling device 100 may be detected by an Indoor Positioning System (IPS). The stapling device 100 may be localized through the techniques such as but not limited to Wi-Fi triangulation and finger printing.

At block 313, a communication interface 133 configured in the stapling device 100 is configured to communicate with one or more external devices 125. The communication interface 133 interfaced with the processing unit 105 communicates the status of the pins in the stapling device 100, the alert signal and the location of the stapling device 100 to the external devices 125. In an embodiment, the external devices 125 are handled by maintenance personnel, and once the exhaustion of pins in the stapling device 100 is communicated, it would be replenished with pins for further usage.

The term stapling device 100 used herein above and below may be used in surgical procedures apart from its regular application of stapling leaf of papers.

In an embodiment of the disclosure, the processing unit 105 of the stapling device 100 for may include specialized processing units such as integrated system (bus) controllers, memory management control units, floating point units, graphics processing units, digital signal processing units, etc. The processing unit may include a microprocessor, such as AMD Athlon, Duron or Opteron, ARM's application, embedded or secure processors, IBM PowerPC, Intel's Core, Itanium, Xeon, Celeron or other line of processors, etc. The processing unit may be implemented using mainframe, distributed processor, multi-core, parallel, grid, or other architectures. Some embodiments may utilize embedded technologies like application-specific integrated circuits (ASICs), digital signal processors (DSPs), Field Programmable Gate Arrays (FPGAs), etc.

In some embodiments, the processing unit 105 may be disposed in communication with one or more memory devices (e.g., RAM, ROM etc.) via a storage interface. The storage interface may connect to memory devices including, without limitation, memory drives, removable disc drives, etc., employing connection protocols such as serial advanced technology attachment (SATA), integrated drive electronics (IDE), IEEE-1394, universal serial bus (USB), fiber channel, small computing system interface (SCSI), etc. The memory drives may further include a drum, magnetic disc drive, magneto-optical drive, optical drive, redundant array of independent discs (RAID), solid-state memory devices, solid-state drives, etc.

In some embodiments, the memory unit 123 may store data as described in this disclosure. Such databases may be implemented as fault-tolerant, relational, scalable, secure databases such as Oracle or Sybase. Alternatively, such databases may be implemented using standardized data structures, such as an array, hash, linked list, struct, structured text file (e.g., XML), table, or as object-oriented databases (e.g., using ObjectStore, Poet, Zope, etc.). Such databases may be consolidated or distributed, sometimes among the various computing units discussed above in this disclosure. It is to be understood that the structure and operation of the any computer or database component may be combined, consolidated, or distributed in any working combination.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., are non-transitory. Examples include random access memory (RAM), read-only memory (ROM), volatile memory, non-volatile memory, hard drives, CD ROMs, DVDs, flash drives, disks, and any other known physical storage media.

Advantages of the embodiment of the present disclosure are illustrated herein.

In an embodiment, the present disclosure provides a method to determine the status or remaining stock of pins in the stapling device.

In an embodiment, the stapling device of the present disclosure, may be used in surgical procedures and for stapling documents.

In an embodiment, the present disclosure provides a method for providing a real time notification of the remaining stock of pins in the stapling device to one or more maintenance personnel of the stapling device, enabling timely replenishment of the stapling device with pins and avoiding discomfort to the users.

In an embodiment, the present disclosure provides a method for notifying the one or more users of the stapling device about the status of the stapling device.

The terms "an embodiment", "embodiment", "embodiments", "the embodiment", "the embodiments", "one or more embodiments", "some embodiments", and "one embodiment" mean "one or more (but not all) embodiments of the invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise.

The terms "a", "an" and "the" mean "one or more", unless expressly specified otherwise.

A description of an embodiment with several components in communication with each other does not imply that all such components are required. On the contrary a variety of optional components are described to illustrate the wide variety of possible embodiments of the invention. When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the invention need not include the device itself.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the embodiments of the present invention are intended to be illustrative, but not limiting, of the scope of the invention, which is set forth in the following claims.

While various aspects and embodiments have been disclosed herein, other aspects and embodiments will be apparent to those skilled in the art. The various aspects and embodiments disclosed herein are for purposes of illustra-

REFERRAL NUMERALS

| Reference Number | Description |
| --- | --- |
| 100 | Stapling device |
| 101 | Activation unit |
| 103 | Detection unit |
| 103a | Image capturing unit |
| 103b | Variable resistor sensor |
| 103c | Proximity sensor |
| 105 | Processing unit |
| 107 | Receiving module |
| 109 | Transmitting module |
| 111 | Detection module |
| 113 | Determination module |
| 115 | Other nodules |
| 117 | User interface |
| 119 | Display with touch screen interface |
| 121 | Position switch |
| 123 | Memory unit |
| 125 | External devices |
| 127 | Pre-configured data |
| 129 | Input data |
| 131 | Other data |
| 133 | Communication interface |
| 135 | Power source/Battery |
| 137 | Physical port |
| 201 | User input button |
| 202 | Arm of the stapling body |
| 203 | Pin slider |
| 204 | Base of the stapling body |
| 205 | Pins of the stapling device |
| 206 | Carrier |
| 207 | Spring |
| 301, 303, 305, 307, 309, 311 and 313 | Steps in flow chart |

We claim:

1. A stapling device, comprising:
    an activation unit configured to sense at least one of a movement of the stapling device, a position of a switch, or a signal from a timer;
    a detection unit communicatively coupled to the activation unit, wherein the detection unit is activated based on a signal from the activation unit to generate an input data;
    a processing unit configured to:
        determine number of pins in the stapling device, by comparing the input data with a pre-configured data; and
        determine a location of the stapling device using an indoor positioning system, the indoor positioning system using at least one of radio waves, magnetic fields, or other sensory information to locate the stapling device; and
    a display unit interfaced with the processing unit, configured to:
        indicate status of the pins in the stapling device, wherein the status is based on the determined number of pins in the stapling device; and
        indicate the location of the stapling device in an alert responsive to determining that the determined number of pins in the stapling device is less than a predetermined threshold.

2. The stapling device as claimed in claim 1, wherein the detection unit is at least one of an image capturing unit and one or more sensors.

3. The stapling device as claimed in claim 2, wherein the one or more sensors includes at least one of a variable resistance sensor and a proximity sensor.

4. The stapling device as claimed in claim 1, wherein the input data is at least one of an image of the pins from the image capturing unit, a signal corresponding to resistance, or a signal to determine proximity from a reference in the stapling device.

5. The stapling device as claimed in claim 1, further comprising a memory unit communicatively coupled to the processing unit, wherein the memory unit stores the pre-configured data.

6. The stapling device as claimed in claim 1, further comprising at least one communication interface interfaced with the processing unit, wherein the at least one communication interface is configured to communicate with one or more external devices.

7. The stapling device as claimed in claim 6, wherein the at least one communication interface communicates at least one of the status of the pins in the stapling device and the location of the stapling device to the one or more external devices.

8. The stapling device as claimed in claim 1, wherein the activation unit identifies movement of the stapling device using an accelerometer.

9. The stapling device as claimed in claim 1, further comprising a power source for supplying power to the processing unit, the detection unit, the activation unit and the display unit.

10. A method for monitoring status of pins in a stapling device, the method comprising:
    activating, by a processing unit of the stapling device, a detection unit upon receiving a signal from an activation unit to generate an input data, wherein the signal is generated when the activation unit senses at least one of a movement of the stapling device, a position of a switch, or a signal from a timer;
    determining, by the processing unit, (i) number of pins in the stapling device by comparing the input data with a pre-configured data and (ii) a location of the stapling device using an indoor positioning system, wherein the indoor positioning system using at least one of radio waves, magnetic fields, or other sensory information to locate the stapling device; and
    indicating, on a display unit of the stapling device, interfaced with the processing unit, (i) status of pins in the stapling device, wherein the status is based on the determined number of pins in the stapling device and (ii) the location of the stapling device in an alert responsive to determining that the determined number of pins in the stapling device is less than a predetermined threshold.

11. The method as claimed in claim 10, wherein the detection unit is at least one of an image capturing unit and one or more sensors.

12. The method as claimed in claim 11, wherein the one or more sensors includes at least one of a variable resistance sensor and a proximity sensor.

13. The method as claimed in claim 10, wherein the input data received by the processing unit, comprises at least one of an image of the pins from the image capturing unit, a signal corresponding to resistance, or a signal to determine proximity from a reference in the stapling device.

14. The method as claimed in claim 10, wherein the pre-configured data is stored in a memory unit.

15. The method as claimed in claim 10, further comprising generating an alert signal when the number of pins in the stapling device is less than a predetermined number.

16. The method as claimed in claim 15, further comprising communicating at least one of the status of the pins, the alert signal, or the location of the stapling device to one or more external devices.

* * * * *